US011890296B2

(12) United States Patent
Kitazawa et al.

(10) Patent No.: US 11,890,296 B2
(45) Date of Patent: Feb. 6, 2024

(54) ANTI-TUMOR AGENT CONTAINING CYTARABINE, ANTI- TUMOR EFFECT ENHANCING AGENT WHICH IS USED IN COMBINATION WITH CYTARABINE, ANTI-TUMOR KIT, AND ANTI-TUMOR AGENT WHICH IS USED IN COMBINATION WITH CYTARABINE (71) Applicant: FUJIFILM Corporation, Tokyo (JP)

(72) Inventors: Satoshi Kitazawa, Ashigarakami-gun (JP); Yukiko Ishii, Ashigarakami-gun (JP); Koichi Saito, Ashigarakami-gun (JP); Shun Matsuda, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 222 days.

(21) Appl. No.: 17/213,567

(22) Filed: Mar. 26, 2021

(65) Prior Publication Data
US 2021/0213040 A1   Jul. 15, 2021

Related U.S. Application Data (63) Continuation of application No. PCT/JP2019/038117, filed on Sep. 27, 2019.

(30) Foreign Application Priority Data

Sep. 28, 2018  (JP) ................. 2018-184218

(51) Int. Cl.
*A01N 43/04* (2006.01)
*A61K 31/70* (2006.01)
*A61K 31/7068* (2006.01)
*A61K 31/455* (2006.01)
*A61K 45/06* (2006.01)

(52) U.S. Cl.
CPC ........ *A61K 31/7068* (2013.01); *A61K 31/455* (2013.01); *A61K 45/06* (2013.01)

(58) Field of Classification Search
None
See application file for complete search history.

(56) References Cited

U.S. PATENT DOCUMENTS

| 2011/0280831 A1 | 11/2011 | Godessart Marina et al. |
| 2015/0157603 A1 | 6/2015 | Higgins et al. |

FOREIGN PATENT DOCUMENTS

| EP | 2 915 804 A1 | 9/2015 |
| JP | 2012-515737 A | 7/2012 |
| JP | 2016-539160 A | 12/2016 |
| JP | 2018-150292 A | 9/2018 |
| WO | 2010/115736 A2 | 10/2010 |
| WO | 2017/037022 A1 | 3/2017 |
| WO | 2017/117372 A1 | 7/2017 |
| WO | 2017/136741 A1 | 8/2017 |
| WO | 2018/160138 A1 | 9/2018 |
| WO | 2019/028171 A1 | 2/2019 |

OTHER PUBLICATIONS

Magina, Kinkini N., et al. "Cytarabine dose in the consolidation treatment of AML: a systematic review and meta-analysis." Blood, The Journal of the American Society of Hematology 130.7 (2017): 946-948.*
Lolli, Marco L., et al. "Use of human dihydroorotate dehydrogenase (hDHODH) inhibitors in autoimmune diseases and new perspectives in cancer therapy." Recent Patents on Anti-Cancer Drug Discovery 13.1 (2018): 86-105.*
Lewis, Timothy A., et al. "Development of ML390: a human DHODH inhibitor that induces differentiation in acute myeloid leukemia." ACS medicinal chemistry letters 7.12 (2016): 1112-1117.*
Brown et al., "Adaptive Reprogramming of De Novo Pyrimidine Synthesis Is a Metabolic Vulnerability in Triple-Negative Breast Cancer", Cancer Discovery, 2017, vol. 7, No. 4, pp. 391-399 (11 pages).
Wu et al., "Pharmacological Inhibition of dihydroorotate dehydrogenase induces apoptosis and differentiation in acute myeloid leukemia cells", Haematologica, 2018, vol. 103, No. 9, pp. 1472-1483 (12 pages).
Janzer et al., "Abstract DDT02-04: Bay 2402234: A novel, selective dihydroorotate dehydrogenase (DHODH) inhibitor for the treatment of myeloid malignancies", Cancer Research, Jul. 2018, vol. 78, Issue 13 Supplement, 2 pages.
Herold et al., "SAMHD1 protects cancer cells from various nucleoside-based antimetabolites", Cell Cycle, 2017, vol. 16, No. 11, pp. 1029-1038 (10 pages).
Kodigepalli et al., "SAMHD1 modulates in vitro proliferation of acute myeloid leukemia-derived THP-1 cells through the PI3K-Akt-p27 axis", Cell Cycle, 2018, vol. 17, No. 9, pp. 1124-1137 (14 pages).
International Search Report dated Nov. 5, 2019, issued by the International Searching Authority in application No. PCT/JP2019/038117.
Written Opinion dated Nov. 5, 2019, issued by the International Searching Authority in application No. PCT/JP2019/038117.
International Preliminary Report on Patentability dated Mar. 23, 2021, issued by the International Bureau in application No. PCT/JP2019/038117.
Yanli Jin et al., "Tenovin-6-mediated inhibition of SIRT1/2 induces apoptosis in acute lymphoblastic leukemia (ALL) cells and eliminates ALL stem/progenitor cells", BMC Cancer, 2015, vol. 15, No. 226, pp. 1-15 (15 pages).

(Continued)

*Primary Examiner* — Patrick T Lewis
(74) *Attorney, Agent, or Firm* — Sughrue Mion, PLLC (57) ABSTRACT An object of the present invention is to provide a combination drug containing cytarabine and a DHODH inhibitor, as a new anti-tumor agent, and to provide an anti-tumor effect enhancing agent which is used in combination with cytarabine, an anti-tumor kit, and an anti-tumor agent which is used in combination with cytarabine. According to the present invention, an anti-tumor agent and an anti-tumor kit containing cytarabine and a dihydroorotate dehydrogenase inhibitor compound are provided.

5 Claims, 4 Drawing Sheets (56) References Cited

OTHER PUBLICATIONS

Marcus J. G. W. Ladds et al., "Exploitation of dihydroorotate dehydrogenase (DHODH) and p53 activation as therapeutic targets: A case study in polypharmacology", J. Biol. Chem., 2020, vol. 295, No. 52, pp. 17935-17949 (15 pages).
Extended European Search Report dated Oct. 28, 2021, issued by the European Patent Office in European application No. 19867799.9.
Office Action dated Feb. 1, 2022, issued by the Japanese Patent Office in Japanese application No. 2020-549428.

* cited by examiner

ANTI-TUMOR AGENT CONTAINING CYTARABINE, ANTI-TUMOR EFFECT ENHANCING AGENT WHICH IS USED IN COMBINATION WITH CYTARABINE, ANTI-TUMOR KIT, AND ANTI-TUMOR AGENT WHICH IS USED IN COMBINATION WITH CYTARABINE

CROSS-REFERENCE TO RELATED APPLICATIONS

This application is a Continuation of PCT International Application No. PCT/JP2019/038117 filed on Sep. 27, 2019, which claims priority under 35 U.S.C § 119(a) to Japanese Patent Application No. 2018-184218 filed on Sep. 28, 2018. Each of the above application(s) is hereby expressly incorporated by reference, in its entirety, into the present application.

BACKGROUND OF THE INVENTION

1. Field of the Invention

The present invention relates to a combination drug containing cytarabine (hereinafter, also referred to as Ara-C) and a dihydroorotate dehydrogenase inhibitor compound (hereinafter, also referred to as a DHODH inhibitor compound).

2. Description of the Related Art

Cytarabine is an anti-tumor agent mainly used in the treatment of acute myelogenous leukemia (AML) and is also antimetabolite. Cytarabine has been used as a standard treatment method for a long time, but there is a demand for a new combination drug and a treatment method that are safer and can be expected to have more therapeutic effects.

On the other hand, a DHODH inhibitor compound is known to have immunosuppressive and antiproliferative effects. Therefore, the DHODH inhibitor compound is expected to be used as a treatment agent for autoimmune diseases such as rheumatoid arthritis, inflammatory diseases, and proliferative diseases.

So far, a combination drug containing cytarabine and an inhibitor compound of MDM2-p53 interaction, a combination drug containing a DHODH inhibitor compound and methotrexate, and the like have been described in the patent literature (JP2016-539160A and JP2012-515737A).

SUMMARY OF THE INVENTION

In recent years, combination therapy has been widely used instead of administering an anti-tumor agent alone. However, in a case where certain drugs are used in combination, it is very difficult to predict whether anti-tumor effects thereof are enhanced or the anti-tumor effects thereof are offset.

An object of the present invention is to provide a combination drug containing cytarabine and a DHODH inhibitor compound as a new anti-tumor agent. Another object of the present invention is to provide an anti-tumor effect enhancing agent which is used in combination with cytarabine, an anti-tumor kit, and an anti-tumor agent which is used in combination with cytarabine.

As a result of intensive studies to solve the above problems, the inventors of the present invention have found that the above-described problems can be solved by using cytarabine and a DHODH inhibitor compound in combination and have completed the present invention.

The present invention provides the followings.

(1) An anti-tumor agent comprising cytarabine; and a dihydroorotate dehydrogenase inhibitor compound.

(2) The anti-tumor agent according to (1), in which the tumor is acute lymphocytic leukemia (ALL), acute myelogenous leukemia (AML), acute promyelocytic leukemia (APL), chronic lymphocytic leukemia (CLL), chronic myelogenous leukemia (CML), chronic neutrophilic leukemia (CNL), acute undifferentiated leukemia (AUL), anaplastic large cell lymphoma (ALCL), prolymphocytic leukemia (PML), juvenile myelomonocytic leukemia (JMML), adult T-cell leukemia/lymphoma (ATL), myelodysplastic syndrome (MDS), myeloproliferative disease (MPD), lymphoblastic lymphoma (LBL), or adult T-cell leukemia/lymphoma (ATL).

(3) The anti-tumor agent according to (1) or (2), in which the tumor is acute lymphocytic leukemia (ALL), acute myelogenous leukemia (AML), acute promyelocytic leukemia (APL), or chronic myelogenous leukemia (CML).

(4) The anti-tumor agent according to any one of (1) to (3), in which the dihydroorotate dehydrogenase inhibitor compound is at least one or more compounds selected from Brequinar, Vidofludimus, Teriflunomide, Leflunomide, N-(2-chloro-6-fluorophenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy} benzamide, (S)-4-chlorophenyl 6-chloro-1-(4-hydroxyphenyl)-3,4-dihydro-1H-pyrido[3,4-h]indol-2 (9H)-carboxylate, or a compound represented by General Formula (1), or a salt thereof, (in the formula, $G^1$ is a CH or nitrogen atom;

$R^1$ is a hydrogen atom, a halogen atom, a $C_{1-6}$ alkyl group which may be substituted, or a $C_{3-8}$ cycloalkyl group which may be substituted; and $R^2$ is an aryl group which may be substituted or a bicyclic heterocyclic group which may be substituted).

(5) The anti-tumor agent according to any one of (1) to (3), in which the dihydroorotate dehydrogenase inhibitor compound is at least one or more compounds selected from ASLAN003 (2-((3,5-difluoro-3'-methoxybiphenyl-4-yl)amino) nicotinic acid) or 5-cyclopropyl-2-((1-phenyl-1H-indol-5-yl)amino) nicotinic acid, or a salt thereof.

(6) The anti-tumor agent according to any one of (1) to (5), in which a daily dose of the cytarabine is 1 g/m² to 10 g/m².

(7) An anti-tumor effect enhancing agent which is used in combination with cytarabine, comprising a dihydroorotate dehydrogenase inhibitor compound.

(8) An anti-tumor kit comprising a pharmaceutical preparation containing cytarabine; and a pharmaceutical preparation containing a dihydroorotate dehydrogenase inhibitor compound.

(9) An anti-tumor agent which is used in combination with cytarabine, comprising a dihydroorotate dehydrogenase inhibitor compound.

(A) A method for treating a tumor, including administering cytarabine and a dihydroorotate dehydrogenase inhibitor compound to a subject.

(B) A combination of cytarabine and a dihydroorotate dehydrogenase inhibitor compound, for use in the treatment of a tumor.

(C) Use of cytarabine and a dihydroorotate dehydrogenase inhibitor compound, for producing an anti-tumor agent.

(D) A method for enhancing an anti-tumor effect, including administering a dihydroorotate dehydrogenase inhibitor compound to a subject in combination with cytarabine.

(E) A dihydroorotate dehydrogenase inhibitor compound for use in combination with cytarabine in a treatment for enhancing an anti-tumor effect.

(F) Use of a dihydroorotate dehydrogenase inhibitor compound for producing an anti-tumor effect enhancing agent which is used in combination with cytarabine.

(G) A method for treating a tumor, including administering a dihydroorotate dehydrogenase inhibitor compound to a subject in combination with cytarabine.

(H) A dihydroorotate dehydrogenase inhibitor compound for use in combination with cytarabine in a treatment of a tumor.

(I) Use of dihydroorotate dehydrogenase inhibitor compound for producing an anti-tumor agent which is used in combination with cytarabine.

The combination drug containing cytarabine and a DHODH inhibitor compound according to the aspect of the present invention is a new anti-tumor agent and has an excellent anti-tumor effect. According to the anti-tumor effect enhancing agent which is used in combination with cytarabine, the anti-tumor kit, and the anti-tumor agent which is used in combination with cytarabine according to the aspect of the present invention, an excellent anti-tumor effect can be exhibited.

In addition, the combination drug containing cytarabine and a DHODH inhibitor compound according to the aspect of the present invention can exhibit a particularly excellent anti-tumor effect in a cancer cell having a high expression of an enzyme (for example, SAMHD1) that converts Ara-CTP, which is an active form of cytarabine, into Ara-C, which is an inactive form. For example, the combination drug containing cytarabine and a DHODH inhibitor compound according to the aspect of the present invention can exhibit a particularly excellent anti-tumor effect on a patient having cancer cells having a high expression of SAMHD1. That is, SAMHD1 is useful as a biomarker in the combined use of cytarabine and a DHODH inhibitor compound according to the aspect of the present invention.

DESCRIPTION OF THE PREFERRED EMBODIMENTS

Hereinafter, the present invention will be described in detail.

As used in the present invention, % means the mass percentage unless otherwise specified. In the present invention, the numerical range indicated by using "to" indicates a range including numerical values described before and after "to" as a minimum value and a maximum value, respectively. In addition, in the present invention, in a case where there are a plurality of substances corresponding to each component in the composition, the amount of each composition in the composition means the total amount of the plurality of substances present in the composition unless otherwise particularly specified.

As used in the present invention, "g/m$^2$" means the dose per body surface area.

Prevention means inhibition of onset of a disease, reduction of the risk of onset of a disease, or delay of onset of a disease.

Treatment means improvement or suppression of progression of a disease or condition of interest.

Treatment means the prevention or treatment of various diseases.

Tumor means a benign or malignant tumor.

A benign tumor means a tumor in which the morphology and sequence of the tumor cell are similar to those of the normal cell from which the tumor cell is derived and which is not invasive or metastatic.

A malignant tumor means a tumor in which the morphology and sequence of a tumor cell are different from those of the normal cell from which the tumor cell is derived and which is invasive or metastatic.

The anti-tumor agent according to the embodiment of the invention is preferably an antineoplastic agent and is preferably used as a treatment agent for hematological cancer.

Examples of the hematological cancer include acute lymphocytic leukemia (ALL), acute myelogenous leukemia (AML), acute promyelocytic leukemia (APL), chronic lymphocytic leukemia (CLL), chronic myelogenous leukemia (CML), chronic neutrophilic leukemia (CNL), acute undifferentiated leukemia (AUL), anaplastic large cell lymphoma (ALCL), prolymphocytic leukemia (PML), juvenile myelomonocytic leukemia (JMML), adult T-cell leukemia (ATL), myelodysplastic syndrome (MDS), myeloproliferative disease (MPD), lymphoblastic lymphoma (LBL), and adult T-cell leukemia/lymphoma (ATL). The anti-tumor agent according to the embodiment of the invention is preferably used as a treatment agent for a cytarabine-adapted disease, more preferably used as a treatment agent for acute lymphocytic leukemia (ALL), acute myelogenous leukemia (AML), acute promyelocytic leukemia (APL), or chronic myelogenous leukemia (CML), and still more preferably used as a treatment agent for acute myelogenous leukemia (AML).

In the combination drug according to the embodiment of the invention, cytarabine and a DHODH inhibitor compound may be provided as the same pharmaceutical composition or may be provided as separate pharmaceutical compositions. "Provided as the same pharmaceutical composition" means that cytarabine and a DHODH inhibitor compound are provided as a form in which they are contained in one pharmaceutical composition.

In the present invention, cytarabine and a DHODH inhibitor compound may be provided as an anti-tumor kit respectively containing a pharmaceutical preparation containing cytarabine and a pharmaceutical preparation containing a DHODH inhibitor compound.

Regarding the excellent anti-tumor effect of the present invention, the presumed mechanism thereof will be described below.

Pyrimidine nucleotide synthesis pathway includes a novel synthesis pathway (a de novo pathway) and a reuse pathway (a salvage pathway). In general, it is known that proliferating cancer cells use not only the salvage pathway but also the de novo pathway to synthesize dCTP, dTTP, CTP, and UTP, which are substrates for DNA and RNA synthesis. In a case where pyrimidine nucleotides are depleted by inhibiting pyrimidine synthesis from the de novo pathway with a DHODH inhibitor compound that works in the de novo pathway, it is presumed that the salvage pathway is activated by the feedback effect. As a result, the conversion efficiency of cytarabine (Ara-C) incorporated into cells by the salvage pathway to the active metabolite Ara-CTP was presumed to increase, and the combination therapy of the DHODH inhibitor compound and cytarabine was presumed to be beneficial in restoring the cytarabine sensitivity of cytarabine-resistant leukemia cells, and thus this study was carried out.

In cytarabine-insensitive THP1 cells, the combined use of a DHODH inhibitor compound and cytarabine significantly increased the cytarabine sensitivity of THP1 cells. When the synergy effect was calculated by Combination Index (CI: a value of 1 or less indicates synergy), it has been found that strong synergy (for example, CI is 0.2 to 0.4) is exhibited. On the other hand, no combined effect was observed in the normal human peripheral blood mononuclear cell PBMC.

When the intracellular CTP concentration was examined, a significant decrease in CTP was observed by the treatment with the DHODH inhibitor compound. On the other hand, when the intracellular Ara-CTP concentration was examined, the Ara-CTP concentration was increased several times by the treatment with the DHODH inhibitor compound, as compared with the Ara-C alone. Based on the above, it is presumed that a DHODH inhibitor compound suppresses the de novo synthesis of pyrimidine, thereby increasing the conversion of Ara-C to Ara-CTP (activating the salvage pathway) in cytarabine-resistant leukemia cells, and is useful for enhancing Ara-C sensitivity. It was suggested that the combination therapy of the DHODH inhibitor compound and cytarabine did not have a significant effect on normal cells and was beneficial in restoring the cytarabine sensitivity of cancer cells.

[1] Cytarabine

The daily dose of cytarabine is preferably 1 g/m$^2$ to 10 g/m$^2$, more preferably 2 g/m$^2$ to 6 g/m$^2$, and still more preferably 3 g/m$^2$ to 5 g/m$^2$.

Cytarabine is preferably administered for 5 days or longer and preferably for 6 days or longer.

Cytarabine is preferably administered in a plurality of cycles, in a case where one cycle is defined by the administration period of 5 to 6 days and the subsequent washout period. The washout period may be 7 to 28 days, 14 to 28 days, or 18 to 24 days.

The plurality of cycles are preferably at least 3 cycles, at least 4 cycles, at least 5 cycles, at least 6 cycles, at least 7 cycles, at least 8 cycles, at least 9 cycles, at least 10 cycles, at least 12 cycles, or at least 15 cycles.

As one example of the administration of cytarabine, 2 g/m$^2$ is mixed with a 5% glucose solution or a physiological saline solution to make 300 to 500 mL for one cycle and can be intravenously administered over 3 hours by intravenous drip infusion every 12 hours for up to 6 days.

Cytarabine can be produced or obtained by using a conventionally known production method or the like.

[2] DHODH Inhibitor Compound

Examples of the DHODH inhibitor compound include Brequinar, Vidofludimus, Teriflunomide, Leflunomide, N-(2-chloro-6-fluorophenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide (a compound described in Example 121 of WO2018/077923A and also referred to as BAY2402234), (S)-4-chlorophenyl 6-chloro-1-(4-hydroxyphenyl)-3,4-dihydro-1H-pyrido[3,4-b]indol-2(9H)-carboxylate (a compound represented by Formula (X) in WO2010/138644A and also referred to as PTC299), and a compound represented by General Formula (1), or a salt thereof.

(in the formula,

G$^1$ is a CH or nitrogen atom;

R$^1$ is a hydrogen atom, a halogen atom, a C$_{1-6}$ alkyl group which may be substituted, or a C$_{3-8}$ cycloalkyl group which may be substituted; and R$^2$ is an aryl group which may be substituted or a bicyclic heterocyclic group which may be substituted).

The halogen atom means a fluorine atom, a chlorine atom, a bromine atom, or an iodine atom.

The C$_{3-6}$ alkyl group means a linear or branched C$_{3-6}$ alkyl group such as a propyl group, an isopropyl group, a butyl group, a sec-butyl group, an isobutyl group, a tert-butyl group, a pentyl group, an isopentyl group, or a hexyl group.

The C$_{1-6}$ alkyl group means a linear or branched C$_{1-6}$ alkyl group such as a methyl group, an ethyl group, a propyl group, an isopropyl group, a butyl group, a sec-butyl group, an isobutyl group, a tert-butyl group, a pentyl group, an isopentyl group, or a hexyl group.

The C$_{2-6}$ alkenyl group means a linear or branched C$_{2-6}$ alkenyl group such as a vinyl group, an allyl group, a propenyl group, an isopropenyl group, a butenyl group, an isobutenyl group, a 1,3-butadienyl group, a pentenyl group, or a hexenyl group.

The $C_{3-8}$ cycloalkyl group means a $C_{3-8}$ cycloalkyl group such as a cyclopropyl group, a cyclobutyl group, a cyclopentyl group, a cyclohexyl group.

The $C_{3-8}$ cycloalkenyl group means a $C_{3-8}$ cycloalkenyl group such as a cyclopropenyl group, a cyclobutenyl group, a cyclopentenyl group, a cyclohexenyl group, or a cyclohexanedienyl group.

The $C_{3-8}$ cycloalkyl $C_{1-6}$ alkyl group means a $C_{3-8}$ cycloalkyl $C_{1-6}$ alkyl group such as a cyclopropylmethyl group, a 2-(cyclopropyl)ethyl group, a cyclobutylmethyl group, a 2-(cyclobutyl)ethyl group, a cyclopentylmethyl group, or a cyclohexylmethyl group.

The aryl group means a phenyl group, a bicyclic condensed hydrocarbon ring group, or a tricyclic condensed hydrocarbon ring group.

The Al $C_{1-6}$ alkyl group means a methoxy, an ethoxy group, a propoxy group, or an isopropoxy group.

The acyl group means a formyl group, a succinyl group, a glutaryl group, a maleoyl group, a phthaloyl group, a $C_{2-12}$ alkanoyl group, an aroyl group, a heterocyclic carbonyl group, or an (α-substituted) aminoacetyl group.

The $C_{2-12}$ alkanoyl group means a linear or branched $C_{2-12}$ alkanoyl group such as an acetyl group, a propionyl group, a valeryl group, an isovaleryl group, or a pivaloyl group.

The aroyl group means a benzoyl group or a naphthoyl group.

The heterocyclic carbonyl group means a nicotinoyl group, a thenoyl group, a pyrrolidinocarbonyl group, or a furoyl group.

The (α-substituted) aminoacetyl group means an (α-substituted) aminoacetyl group, in which the N-terminal may be protected and which is derived from amino acids (examples thereof include glycine, alanine, valine, leucine, isoleucine, serine, threonine, cysteine, methionine, aspartic acid, glutamic acid, asparagine, glutamine, arginine, lysine, histidine, hydroxylysine, phenylalanine, tyrosine, tryptophan, proline, and hydroxyproline).

The bicyclic condensed hydrocarbon ring group means a bicyclic condensed hydrocarbon ring in which a part of a group such as a pentarenyl group, an indanyl group, an indenyl group, or a naphthyl group may be hydrogenated.

The tricyclic condensed hydrocarbon ring group means a tricyclic condensed hydrocarbon ring in which a part of a group such as a biphenylenyl group, an acenaphthenyl group, an acenaphthylenyl group, a fluorenyl group, a phenalenyl group, a phenanthrenyl group, or an anthracenyl group may be hydrogenated.

The heterocyclic group means a monocyclic heterocyclic group, a bicyclic heterocyclic group, or a tricyclic heterocyclic group.

The monocyclic heterocyclic group means a monocyclic nitrogen-containing heterocyclic group, a monocyclic oxygen-containing heterocyclic group, a monocyclic sulfur-containing heterocyclic group, a monocyclic nitrogen-containing and oxygen-containing heterocyclic group, or a monocyclic nitrogen-containing and sulfur-containing heterocyclic group.

The monocyclic oxygen-containing heterocyclic group means a tetrahydrofuranyl group, a furanyl group, a tetrahydropyranyl group, a dihydropyranyl group, or a pyranyl group.

The monocyclic sulfur-containing heterocyclic group means a thienyl group.

The monocyclic nitrogen-containing and oxygen-containing heterocyclic group means a monocyclic nitrogen-containing and oxygen-containing heterocyclic group containing only nitrogen atoms and oxygen atoms as heteroatoms forming a ring of a group such as an oxazolyl group, isooxazolyl group, an oxadiazolyl group, or a morpholinyl group.

The monocyclic nitrogen-containing and sulfur-containing heterocyclic group means a monocyclic nitrogen-containing and sulfur-containing heterocyclic group containing only nitrogen atoms and sulfur atoms as heteroatoms forming a ring of a group such as thiazolyl group, an isothiazolyl group, a thiadiazolyl group, a thiomorpholinyl group, a 1-oxide thiomorpholinyl group, or a 1,1-dioxide thiomorpholinyl group.

The bicyclic heterocyclic group means a bicyclic nitrogen-containing heterocyclic group, a bicyclic oxygen-containing heterocyclic group, a bicyclic sulfur-containing heterocyclic group, a bicyclic nitrogen-containing and oxygen-containing heterocyclic group, or a bicyclic nitrogen-containing and sulfur-containing heterocyclic group.

The bicyclic nitrogen-containing heterocyclic group means a bicyclic nitrogen-containing heterocyclic group containing only nitrogen atoms as heteroatoms forming a ring of a group such as an indolinyl group, an indolyl group, an isoindolinyl group, an isoindolyl group, a pyrrolopyridinyl group, an indazolyl group, a benzimidazolyl group, a benzotriazolyl group, a tetrahydroquinolinyl group, a dihydroquinolinyl group, a quinolinyl group, a tetrahydroquinolinyl group, a tetrahydroisoquinolinyl group, an isoquinolinyl group, a dihydroquinazolinyl group, a cinnolinyl group, a phthalazinyl group, a quinazolinyl group, a dihydroquinoxalinyl group, a quinoxalinyl group, a naphthyridinyl group, a prynyl group, a pteridinyl group, or a quinuclidinyl group.

The bicyclic oxygen-containing heterocyclic group means a bicyclic oxygen-containing heterocyclic group containing only oxygen atoms as heteroatoms forming a ring of a group such as a 2,3-dihydrobenzofuranyl group, a benzofuranyl group, an isobenzofuranyl group, a chromanyl group, a chromenyl group, an isochromanyl group, a 1,3-benzodioxolyl group, a 1,3-benzodioxanyl group, or a 1,4-benzodioxanyl group.

The bicyclic sulfur-containing heterocyclic group means a bicyclic sulfur-containing heterocyclic group containing only sulfur atoms as heteroatoms forming a ring of a group such as a 2,3-dihydrobenzothienyl group or a benzothienyl group.

The bicyclic nitrogen-containing and oxygen-containing heterocyclic group means a bicyclic nitrogen-containing and oxygen-containing heterocyclic group containing only nitrogen atoms and oxygen atoms as heteroatoms forming a ring of a group such as a dihydrobenzoxazolyl group, a benzoxazolyl group, a benzisooxazolyl group, a benzoxadiazolyl group, a benzomorpholinyl group, a dihydropyranopyridyl group, a dihydrodioxynopyridyl group, or a dihydropyridooxadinyl group.

The bicyclic nitrogen-containing and sulfur-containing heterocyclic group means a bicyclic nitrogen-containing and sulfur-containing heterocyclic group containing nitrogen atoms and sulfur atoms as heteroatoms forming a ring of a group such as a dihydrobenzothiazolyl group, a benzothiazolyl group, a benzisothiazolyl group, or a benzothiadiazolyl group.

The heterocyclic $C_{1-6}$ alkyl group means a monocyclic nitrogen-containing heterocyclic $C_{1-6}$ alkyl group such as an azetidinylmethyl group, an azetidinylethyl group, a pyrrolidinylmethyl group, a pyrrolidinylethyl group, a piperidylmethyl group, a piperidylethyl group, a pyridylmethyl group, a pyridylethyl group, an imidazolylmethyl group, an imidazolylethyl group, a piperazinylmethyl group, or piperazinylethyl group; a monocyclic oxygen-containing heterocyclic $C_{1-6}$ alkyl group such as a tetrahydrofuranylmethyl group or a tetrahydropyranylmethyl group; a monocyclic sulfur-containing heterocyclic $C_{1-6}$ alkyl group such as a thienylmethyl group; a monocyclic nitrogen-containing and oxygen-containing heterocyclic $C_{1-6}$ alkyl group such as an oxazolylmethyl group, an oxazolylethyl group, an isooxazolylmethyl group, an isooxazolylethyl group, a morpholinylmethyl group, or a morpholinylethyl group; a monocyclic nitrogen-containing and sulfur-containing heterocyclic $C_{1-6}$ alkyl group such as a thiazolylmethyl group, thiazolylethyl group, an isothiazolylmethyl group, or an isothiazolylethyl group; a bicyclic nitrogen-containing heterocyclic $C_{1-6}$ alkyl group such as an indolylmethyl group, an indolylethyl group, a benzimidazolylmethyl group, a benzimidazolylethyl group, a quinolylmethyl, or a quinolylethyl group; a bicyclic oxygen-containing heterocyclic $C_{1-6}$ alkyl group such as a benzofuranylmethyl group, an isobenzofuranylmethyl group, or a chromanylmethyl group; a bicyclic sulfur-containing heterocyclic $C_{1-6}$ alkyl group such as a benzothienylmethyl group; a bicyclic nitrogen-containing and oxygen-containing heterocyclic $C_{1-6}$ alkyl group such as a benzoxazolylmethyl or a benzisoxazolylmethyl group; a bicyclic nitrogen-containing and sulfur-containing heterocyclic $C_{1-6}$ alkyl group such as a benzothiazolylmethyl group or a benzisothiazolylmethyl group; a tricyclic nitrogen-containing heterocyclic $C_{1-6}$ alkyl group such as a carbazolylmethyl group; tricyclic oxygen-containing heterocyclic $C_{1-6}$ alkyl group such as a xanthenylmethyl group; and a tricyclic sulfur-containing heterocyclic $C_{1-6}$ alkyl group such as a thianthrenylmethyl group.

The compound represented by General Formula (1) is preferably a compound described as follows.

$G^1$ is CH or a nitrogen atom, preferably a nitrogen atom.

$R^1$ is a hydrogen atom, a halogen atom, a $C_{1-6}$ alkyl group which may be substituted, or a $C_{3-8}$ cycloalkyl group which may be substituted, more preferably a hydrogen atom, a chlorine atom, or a $C_{3-8}$ cycloalkyl group which may be substituted, still more preferably a hydrogen atom, a chlorine atom, or cyclopropyl group which may be substituted, and even still more preferably a hydrogen atom, a chlorine atom, or a cyclopropyl group.

Examples of the substituent of the $C_{1-6}$ alkyl group and $C_{3-8}$ cycloalkyl group of $R^1$ include at least one or more groups selected from the substituent group α.

$R^2$ is an aryl group which may be substituted or a bicyclic heterocyclic group which may be substituted. Examples of the substituent of the aryl group and bicyclic heterocyclic group of $R^2$ include at least one or more groups selected from the substituent group α.

$R^2$ is preferably an aryl group which may be substituted with at least one or more groups selected from the substituent group α or preferably a group represented by General Formula (3-1) or (3-2).

(3-1)

(3-2)

In the formula, $X^{1a}$, $X^{2a}$, and $X^{3a}$ are the same or different from each other, and are $CR^5$ or a nitrogen atom; $X^4$ is CH or a nitrogen atom; $R^{4a}$ is a $C_{1-6}$ alkyl group which may be substituted, a $C_{3-8}$ cycloalkyl $C_{1-6}$ alkyl group which may be substituted, an aryl group which may be substituted, or an Al $C_{1-6}$ alkyl group which may be substituted; $R^5$ is a hydrogen atom, a halogen atom, a $C_{1-6}$ alkyl group which may be substituted, a $C_{2-6}$ alkenyl group which may be substituted, a $C_{3-8}$ cycloalkyl group which may be substituted, a $C_{3-8}$ cycloalkenyl group which may be substituted, a $C_{3-8}$ cycloalkyl $C_{1-6}$ alkyl group which may be substituted, an aryl group which may be substituted, a heterocyclic group which may be substituted, or an Al $C_{1-6}$ alkyl group which may be substituted.

Alternatively, in a case where $G^1$ is CH and $R^1$ is a chlorine atom or a $C_{3-8}$ cycloalkyl group which may be substituted, $R^2$ is preferably a group represented by General Formula (4-1) or (4-2).

(4-1)

(4-2)

In the formula, $X^{1b}$, $X^{2b}$, and $X^{3b}$ are the same or different from each other, and are CH or a nitrogen atom; $R^{4b}$ is an aryl group which may be substituted or a group represented by an Al $C_{1-6}$ alkyl group which may be substituted.

The $C_{1-6}$ alkyl group of $R^{4a}$ is preferably a $C_{1-4}$ alkyl group, more preferably a methyl group, an ethyl group, or an isopropyl group, and still more preferably a methyl group or an isopropyl group.

The $C_{3-8}$ cycloalkyl $C_{1-6}$ alkyl group of $R^{4a}$ is preferably a $C_{3-6}$ cycloalkyl $C_{1-3}$ alkyl group and more preferably a cyclobutylmethyl group, a cyclopentylmethyl group, or a cyclohexylmethyl group.

The aryl group of $R^{4a}$ is preferably a phenyl group.

The Al $C_{1-6}$ alkyl group of $R^{4a}$ is preferably a phenylmethyl group.

Examples of the substituent of the $C_{1-6}$ alkyl group, $C_{3-8}$ cycloalkyl $C_{1-6}$ alkyl group, aryl group, and Al $C_{1-6}$ alkyl group of $R^{4a}$ include at least one or more groups selected from the substituent group α.

Examples of the halogen atom of $R^5$ is preferably a fluorine atom.

The $C_{1-6}$ alkyl group of $R^5$ is preferably a $C_{1-4}$ alkyl group and more preferably a methyl group, an ethyl group, or a propyl group.

The $C_{2-6}$ alkenyl group of $R^5$ is preferably a $C_{2-4}$ alkenyl group, more preferably a 1-propenyl group or a 2-propenyl group, and still more preferably a 1-propenyl group.

The $C_{3-8}$ cycloalkyl group of $R^5$ is preferably a $C_{3-6}$ cycloalkyl group.

The $C_{3-8}$ cycloalkenyl group of $R^5$ is preferably a $C_{3-6}$ cycloalkenyl group and more preferably a cyclohexenyl group.

The $C_{3-8}$ cycloalkyl $C_{1-6}$ alkyl group of $R^5$ is preferably a $C_{3-6}$ cycloalkyl $C_{1-3}$ alkyl group.

The aryl group of $R^5$ is preferably a phenyl group.

The Al $C_{1-6}$ alkyl group of $R^5$ is preferably a phenyl $C_{1-6}$ alkyl group.

Examples of the substituents of the $C_{1-6}$ alkyl group of $R^5$, the $C_{2-6}$ alkenyl group of $R^5$, the $C_{3-8}$ cycloalkyl group of $R^5$, the $C_{3-8}$ cycloalkenyl group of $R^5$, the $C_{3-8}$ cycloalkyl $C_{1-6}$ alkyl group of $R^5$, the aryl group of $R^5$, the heterocyclic group of $R^5$, and the Al $C_{1-6}$ alkyl group of $R^5$ include at least one or more groups selected from the substituent group α.

The aryl group of $R^{4b}$ is preferably a phenyl group.

The Al $C_{1-6}$ alkyl group of $R^{4b}$ is preferably a phenylmethyl group.

Substituents of the aryl group of $R^{4b}$ and the Al $C_{1-6}$ alkyl group include at least one or more groups selected from the substituent group α.

$R^2$ is more preferably a group represented by General Formula (5-1) or (5-2).

(5-1)

(5-2)

In the formula, $R^{4c}$ is a $C_{1-6}$ alkyl group which may be substituted or an aryl group which may be substituted; $R^{5c}$'s are each independently a hydrogen atom, a halogen atom, an aryl group which may be substituted, or a heterocyclic group which may be substituted.

Alternatively, in a case where $G^1$ is CH and $R^1$ is a chlorine atom or a $C_{3-8}$ cycloalkyl group which may be substituted, $R^2$ is more preferably a group represented by General Formula (6).

(6)

In the formula, $R^{4d}$ is an aryl group which may be substituted or an Al $C_{1-6}$ alkyl group which may be substituted.

The $C_{1-6}$ alkyl group of $R^{4c}$ is preferably a $C_{1-4}$ alkyl group, more preferably a methyl group, an ethyl group, or an isopropyl group, and still more preferably a methyl group or an isopropyl group.

The aryl group of $R^{4c}$ is preferably a phenyl group.

Examples of the substituent of the $C_{1-6}$ alkyl group and aryl group of $R^{4c}$ include at least one or more groups selected from the substituent group α.

The halogen atom of $R^{5c}$ is preferably a fluorine atom.

The aryl group of $R^{5c}$ is preferably a phenyl group.

Examples of the substituent of the aryl group and heterocyclic group of $R^{5c}$ include at least one or more groups selected from the substituent group α.

The aryl group of $R^{4d}$ is preferably a phenyl group.

The Al $C_{1-6}$ alkyl group of $R^{4d}$ is preferably a phenylmethyl group.

Examples of the substituent of the aryl group of $R^{4d}$ and the Al $C_{1-6}$ alkyl group include at least one or more groups selected from the substituent group α.

It is more preferable that $R^2$ is a group represented by General Formula (7).

(7)

In the formula, $R^{4c}$ is a $C_{1-6}$ alkyl group which may be substituted or an aryl group which may be substituted; $R^{5c}$'s are each independently a hydrogen atom, a halogen atom, an aryl group which may be substituted, or a heterocyclic group which may be substituted.

However, in this case, $G^1$ is preferably a nitrogen atom.

Substituent group α: a halogen atom, a hydroxyl group which may be protected, a carboxyl group which may be protected, an amino group which may be protected, a nitro group, a cyano group, a carbamoyl group which may be substituted with at least one or more groups selected from the substituent group β, a $C_{1-6}$ alkyl group which may be substituted with at least one or more groups selected from the substituent group β, a $C_{2-6}$ alkenyl group which may be substituted with at least one or more groups selected from the substituent group β, a $C_{3-8}$ cycloalkyl group which may be substituted with at least one or more groups selected from the substituent group β, a $C_{1-6}$ alkoxy group which may be substituted with at least one or more groups selected from the substituent group β, an acyl group which may be substituted with at least one or more groups selected from the substituent group β, an alkoxycarbonyl group which may be substituted with at least one or more groups selected from the substituent group β, a $C_{1-6}$ alkylamino group which may be substituted with at least one or more groups selected from the substituent group β, a di($C_{1-6}$ alkyl)amino group which may be substituted with at least one or more groups selected from the substituent group β, a $C_{1-6}$ alkylthio group which may be substituted with at least one or more groups selected from the substituent group β, a $C_{1-6}$ alkylsulfonyl group which may be substituted with at least one or more groups selected from the substituent group β, an aryl group which may be substituted with at least one or more groups selected from the substituent group β, a heterocyclic group which may be substituted with at least one or more groups selected from the substituent group β, and an oxo group Substituent group β: a halogen atom, a hydroxyl group which may be protected, a carboxyl group which may be protected, an amino group which may be protected, a carbamoyl group, a $C_{1-6}$ alkyl group which may be substituted with a halogen atom, a $C_{1-6}$ alkoxy group which may be substituted with a halogen atom, a $C_{1-6}$ alkylamino group, a di($C_{1-6}$ alkyl)amino group, a heterocyclic group, and an oxo group.

Examples of the preferred compound of the compound represented by General Formula (1) include the followings.

ASLAN003 (2-((3,5-difluoro-3'-methoxybiphenyl-4-yl) amino) nicotinic acid), 5-chloro-2-((1-phenyl-1H-indol-5-yl)amino) benzoic acid, 2-((1-benzyl-1H-indol-5-yl)amino)-5-cyclopropyl benzoic acid, 2-((1-benzyl-1H-pyrrolo(2,3-b)pyridine-5-yl)amino)-5-cyclopropyl benzoic acid, 2-((1-benzyl-1H-indazol-5-yl)amino)-5-cyclopropylbenzoate, 5-chloro-2-((1-(3-(trifluoromethyl)phenyl)-1H-indol-5-yl) amino) benzoic acid, 5-cyclopropyl-2-((1-phenyl-1H-indol-5-yl)amino) benzoic acid, 2-((1-benzyl-1H-indol-5-yl) amino)-5-cyclopropyl nicotinic acid, 5-cyclopropyl-2-((1-phenyl-1H-indol-5-yl)amino) nicotinic acid, 5-cyclopropyl-2-((1-(4-(trifluoromethyl)phenyl)-1H-indol-5-yl)amino) benzoic acid, 2-((3-benzyl-2-oxo-2,3-dihydrobenzo[d]thiazol-6-yl)amino)-5-cyclopropyl nicotinic acid, 2-((1-(cyclohexylmethyl)-1H-indol-5-yl)amino)-5-cyclopropyl nicotinic acid, 2-((1-(cyclobutylmethyl)-1H-indol-5-yl)amino)-5-cyclopropyl nicotinic acid, 5-cyclopropyl-2-((5-phenylnaphthalen-1-yl)amino) nicotinic acid, 5-cyclopropyl-2-(1-methyl-3-phenyl-1H-indol-5-yl)amino) nicotinic acid, 5-cyclopropyl-2-((5-phenylnaphthalen-2-yl) amino) nicotinic acid, 5-cyclopropyl-2-((8-phenylnaphthalen-2-yl)amino) nicotinic acid, 5-cyclopropyl-2-((1-methyl-7-phenyl-1H-indol-5-yl)amino) nicotinic acid, 5-cyclopropyl-2-((1-(3-fluorophenyl)-1H-indol-5-yl)amino) nicotinic acid, 5-cyclopropyl-2-((1-(4-fluorophenyl)-1H-indol-5-yl)amino) nicotinic acid, 5-cyclopropyl-2-((1-(3-fluorobenzyl)-1H-indol-5-yl)amino) nicotinic acid, 5-cyclopropyl-2-((1-phenyl-1H-indol-4-yl)amino) nicotinic acid, 2-((1-(cyclohexylmethyl)-1H-indazol-5-yl)amino)-5-cyclopropyl nicotinic acid, 2-((1-benzyl-1H-pyrrolo(2,3-b)pyridine-5-yl)amino)-5-cyclopropyl nicotinic acid, 2-((1-benzyl-6-fluoro-1H-indol-5-yl)amino)-5-cyclopropyl nicotinic acid, 5-cyclopropyl-2-((1-(3-(trifluoromethyl)benzyl)-1H-indol-5-yl)amino) nicotinic acid, 2-((1-benzyl-4,6-difluoro-1H-indol-5-yl)amino)-5-cyclopropyl nicotinic acid, 2-((1-(3-chlorobenzyl)-1H-indol-5-yl)amino)-5-cyclopropyl nicotinic acid, 5-cyclopropyl-2-((7-(2-fluorophenyl)-1-methyl-1H-indol-5-yl)amino) nicotinic acid, 5-cyclopropyl-2-((7-(3-fluorophenyl)-1-methyl-1H-indol-5-yl)amino) nicotinic acid, 5-cyclopropyl-2-((7-(4-fluorophenyl)-1-methyl-1H-indol-5-yl)amino) nicotinic acid, (E)-5-cyclopropyl-2-((7-(3-methoxypropyl-1-en-1-yl)-1-methyl-1H-indol-5-yl)amino) nicotinic acid, 5-cyclopropyl-2-((7-(3-methoxypropyl))-1-methyl-1H-indol-5-yl)amino) nicotinic acid, (E)-5-cyclopropyl-2-((7-(2-cyclopropylvinyl)-1-methyl-1H-indol-5-yl)amino) nicotinic acid, 5-cyclopropyl-2-((7-(2-cyclopropylethyl)-1-methyl-1H-indol-5-yl)amino) nicotinic acid, 5-cyclopropyl-2-((7-(3,6-dihydro-2H-pyran-4-yl)-1-methyl-1H-indol-5-yl)amino) nicotinic acid, 5-cyclopropyl-2-((1-phenylisoquinolin-6-yl)amino) nicotinic acid, 5-cyclopropyl-2-((1-methyl-7-(2-trifluoromethyl)phenyl)-1H-indol-5-yl)amino) nicotinic acid, 5-cyclopropyl-2-((1-methyl-7-(3-trifluoromethyl)phenyl)-1H-indol-5-yl) amino) nicotinic acid, 5-cyclopropyl-2-((1-methyl-7-(4-trifluoromethyl)phenyl)-1H-indol-5-yl)amino) nicotinic acid, 5-cyclopropyl-2-((1-isobutyl-3-methyl-1H-indol-5-yl) amino) nicotinic acid, 2-((7-(2-cyanophenyl)-1-methyl-1H-indol-5-yl)amino)-5-cyclopropyl nicotinic acid, 2-((7-(4-cyanophenyl)-1-methyl-1H-indol-5-yl)amino)-5-cyclopropyl nicotinic acid, 2-((7-(3-chlorophenyl)-1-methyl-1H-indol-5-yl)amino)-5-cyclopropyl nicotinic acid, 2-((7-(4-chlorophenyl)-1-methyl-1H-indol-5-yl)amino)-5-cyclopropyl nicotinic acid, 5-cyclopropyl-2-((1-methyl-7-(2-(trifluoromethoxy)phenyl)-1H-indol-5-yl)amino) nicotinic acid, 5-cyclopropyl-2-((1-methyl-7-(3-(trifluoromethoxy)phenyl)-1H-indol-5-yl)amino) nicotinic acid, 5-cyclopropyl-2-((1-methyl-7-(4-(trifluoromethoxy) phenyl)-1H-indol-5-yl)amino) nicotinic acid, 2-((7-cyclohex-1-en-1-yl)-1-methyl-1H-indol-5-yl)amino)-5-cyclopropyl nicotinic acid, 2-((1-benzyl-6-methyl-1H-indol-5-yl) amino)-5-cyclopropyl nicotinic acid, 5-cyclopropyl-2-((1-(3,5-difluorobenzyl)-1H-indol-5-yl)amino) nicotinic acid, 2-((1-(cyclopentylmethyl)-1H-indol-4-yl)amino)-5-cyclopropyl nicotinic acid, 5-cyclopropyl-2-((2-oxo-1-phenyl-1,2-dihydroquinolin-5-yl)amino) benzoic acid, and 2-((1-benzyl-4-methyl-1H-indol-5-yl)amino)-5-cyclopropyl nicotinic acid.

The compound represented by General Formula (1) is preferably at least one or more compounds selected from ASLAN003 (2-((3,5-difluoro-3'-methoxybiphenyl-4-yl) amino) nicotinic acid), 5-chloro-2-((1-phenyl-1H-indol-5-yl)amino) benzoic acid, 2-((1-benzyl-1H-indol-5-yl)amino)-5-cyclopropyl benzoic acid, 2-((1-benzyl-1H-pyrrolo(2,3-b)pyridine-5-yl)amino)-5-cyclopropyl benzoic acid, 2-((1-benzyl-1H-indazol-5-yl)amino)-5-cyclopropylbenzoate, 5-chloro-2-((1-(3-(trifluoromethyl)phenyl)-1H-indol-5-yl) amino) benzoic acid, 5-cyclopropyl-2-((1-phenyl-1H-indol-5-yl)amino) benzoic acid, 2-((1-benzyl-1H-indol-5-yl) amino)-5-cyclopropyl nicotinic acid, 5-cyclopropyl-2-((1-phenyl-1H-indol-5-yl)amino) nicotinic acid, 5-cyclopropyl-2-((1-(4-(trifluoromethyl)phenyl)-1H-indol-5-yl)amino) benzoic acid, 2-((1-(cyclohexylmethyl)-1H-indol-5-yl) amino)-5-cyclopropyl nicotinic acid, 2-((1-(cyclobutylmethyl)-1H-indol-5-yl)amino)-5-cyclopropyl nicotinic acid, 5-cyclopropyl-2-((5-phenylnaphthalen-1-yl)amino) nicotinic acid, 5-cyclopropyl-2-((5-phenylnaphthalen-2-yl) amino) nicotinic acid, 5-cyclopropyl-2-((8-phenylnaphthalen-2-yl)amino) nicotinic acid, 5-cyclopropyl-2-((1-methyl-7-phenyl-1H-indol-5-yl)amino) nicotinic acid, 5-cyclopropyl-2-((1-(3-fluorophenyl)-1H-indol-5-yl)amino) nicotinic acid, 5-cyclopropyl-2-((1-(4-fluorophenyl)-1H-indol-5-yl)amino) nicotinic acid, 5-cyclopropyl-2-((1-phenyl-1H-indol-4-yl)amino) nicotinic acid, 2-((1-(cyclohexylmethyl)-1H-indazol-5-yl)amino)-5-cyclopropyl nicotinic acid, 2-((1-benzyl-1H-pyrrolo(2,3-b)pyridine-5-yl)amino)-5-cyclopropyl nicotinic acid, 2-((1-benzyl-6-fluoro-1H-indol-5-yl)amino)-5-cyclopropyl nicotinic acid, 5-cyclopropyl-2-((1-(3-(trifluoromethyl)benzyl)-1H-indol-5-yl)amino) nicotinic acid, 2-((1-benzyl-4,6-difluoro-1H-indol-5-yl) amino)-5-cyclopropyl nicotinic acid, 2-((1-(3-chlorobenzyl)-1H-indol-5-yl)amino)-5-cyclopropyl nicotinic acid, 5-cyclopropyl-2-((7-(2-fluorophenyl-1-methyl-1H-indol-5-yl)amino) nicotinic acid, 5-cyclopropyl-2-((7-(3-fluorophenyl)-1-methyl-1H-indol-5-yl)amino) nicotinic acid, 5-cyclopropyl-2-((7-(4-fluorophenyl)-1-methyl-1H-indol-5-yl) amino) nicotinic acid, (E)-5-cyclopropyl-2-((7-(3-methoxypropyl-1-en-1-yl)-1-methyl-1H-indol-5-yl)amino) nicotinic acid, 5-cyclopropyl-2-((7-(3-methoxypropyl))-1-methyl-1H-indol-5-yl)amino) nicotinic acid, (E)-5-cyclopropyl-2-((7-(2-cyclopropylvinyl)-1-methyl-1H-indol-5-yl) amino) nicotinic acid, 5-cyclopropyl-2-((7-(2-cyclopropylethyl)-1-methyl-1H-indol-5-yl)amino) nicotinic acid, 5-cyclopropyl-2-((7-(3,6-dihydro-2H-pyran-4-yl)-1-methyl-1H-indol-5-yl)amino) nicotinic acid, 5-cyclopropyl-2-((1-phenylisoquinolin-6-yl)amino) nicotinic acid, 5-cyclopropyl-2-((1-methyl-7-(2-trifluoromethyl)phenyl)-1H-indol-5-yl)amino) nicotinic acid, 5-cyclopropyl-2-((1-methyl-7-(3-trifluoromethyl)phenyl)-1H-indol-5-yl)amino) nicotinic acid, 5-cyclopropyl-2-((1-methyl-7-(4-trifluoromethyl)phenyl)-1H-indol-5-yl)amino) nicotinic acid, 5-cyclopropyl-2-((1-isobutyl-3-methyl-1H-indol-5-yl)amino) nicotinic acid, 2-((7-(2-cyanophenyl)-1-methyl-1H-indol-5-yl)amino)-5-cyclopropyl nicotinic acid, 2-((7-(4-cyanophenyl)-1-methyl-1H-indol-5-yl)amino)-5-cyclopropyl nicotinic acid, 2-((7-(3-chlorophenyl)-1-methyl-1H-indol-5-yl)amino)-5-cyclopropyl nicotinic acid, 2-((7-(4-chlorophenyl)-1-methyl-1H-indol-5-yl)amino)-5-cyclopropyl nicotinic acid, 5-cyclopropyl-2-((1-methyl-7-(2-(trifluoromethoxy)phenyl)-1H-indol-5-yl)amino) nicotinic acid, 5-cyclopropyl-2-((1-methyl-7-(3-(trifluoromethoxy)phenyl)-1H-indol-5-yl)amino) nicotinic acid, 5-cyclopropyl-2-((1-methyl-7-(4-(trifluoromethoxy)phenyl)-1H-indol-5-yl)amino) nicotinic acid, 2-((7-cyclohex-1-en-1-yl)-1-methyl-1H-indol-5-yl)amino)-5-cyclopropyl nicotinic acid, 2-((1-benzyl-6-methyl-1H-indol-5-yl)amino)-5-cyclopropyl nicotinic acid, 5-cyclopropyl-2-((1-(3,5-difluorobenzyl)-1H-indol-5-yl)amino) nicotinic acid, 2-((1-(cyclopentylmethyl)-1H-indol-4-yl)amino)-5-cyclopropyl nicotinic acid, 5-cyclopropyl-2-((2-oxo-1-phenyl-1,2-dihydroquinolin-5-yl)amino) benzoic acid, or 2-((1-benzyl-4-methyl-1H-indol-5-yl)amino)-5-cyclopropyl nicotinic acid, or a salt thereof.

The compound represented by General Formula (1) is preferably at least one or more compounds selected from ASLAN003 (2-((3,5-difluoro-3'-methoxybiphenyl-4-yl)amino) nicotinic acid), 2-((1-benzyl-1H-indol-5-yl)amino)-5-cyclopropyl benzoic acid, 5-cyclopropyl-2-((1-phenyl-1H-indol-5-yl)amino) nicotinic acid, 5-cyclopropyl-2-((1-(4-(trifluoromethyl)phenyl)-1H-indol-5-yl)amino) benzoic acid, 5-cyclopropyl-2-((5-phenylnaphthalen-1-yl)amino) nicotinic acid, 5-cyclopropyl-2-((5-phenylnaphthalen-2-yl) amino) nicotinic acid, 5-cyclopropyl-2-((1-methyl-7-phenyl-1H-indol-5-yl)amino) nicotinic acid, 5-cyclopropyl-2-((1-(4-fluorophenyl)-1H-indol-5-yl)amino) nicotinic acid, 2-((1-benzyl-4,6-difluoro-1H-indol-5-yl)amino)-5-cyclopropyl nicotinic acid, 5-cyclopropyl-2-((7-(2-fluorophenyl)-1-methyl-1H-indol-5-yl)amino) nicotinic acid, 5-cyclopropyl-2-((7-(3-fluorophenyl)-1-methyl-1H-indol-5-yl)amino) nicotinic acid, 5-cyclopropyl-2-((7-(4-fluorophenyl)-1-methyl-1H-indol-5-yl)amino) nicotinic acid, 5-cyclopropyl-2-((7-(3,6-dihydro-2H-pyran-4-yl)-1-methyl-1H-indol-5-yl) amino) nicotinic acid, 5-cyclopropyl-2-((1-methyl-7-(2-trifluoromethyl)phenyl)-1H-indol-5-yl)amino) nicotinic acid, 5-cyclopropyl-2-((1-methyl-7-(3-trifluoromethyl)phenyl)-1H-indol-5-yl)amino) nicotinic acid, 5-cyclopropyl-2-((1-methyl-7-(4-trifluoromethyl)phenyl)-1H-indol-5-yl) amino) nicotinic acid, 2-((7-(4-cyanophenyl)-1-methyl-1H-indol-5-yl)amino)-5-cyclopropyl nicotinic acid, 2-((7-(3-chlorophenyl)-1-methyl-1H-indol-5-yl)amino)-5-cyclopropyl nicotinic acid, 2-((7-(4-chlorophenyl)-1-methyl-1H-indol-5-yl)amino)-5-cyclopropyl nicotinic acid, 5-cyclopropyl-2-((1-methyl-7-(2-(trifluoromethoxy)phenyl)-1H-indol-5-yl)amino) nicotinic acid, 5-cyclopropyl-2-((1-methyl-7-(3-(trifluoromethoxy)phenyl)-1H-indol-5-yl) amino) nicotinic acid, 5-cyclopropyl-2-((1-methyl-7-(4-(trifluoromethoxy)phenyl)-1H-indol-5-yl)amino) nicotinic acid, or 2-((7-cyclohex-1-en-1-yl)-1-methyl-1H-indol-5-yl) amino)-5-cyclopropyl nicotinic acid, or a salt thereof.

Examples of the salt of the compound of General Formula (1) include salts of basic groups such as generally known amino groups and acidic groups such as phenolic hydroxyl groups or carboxyl groups.

Examples of the salt of the basic group include a salt with a mineral acid such as hydrochloric acid, hydrobromic acid, nitric acid, or sulfuric acid; a salt with an organic carboxylic acid such as formic acid, acetic acid, citric acid, oxalic acid, fumaric acid, maleic acid, succinic acid, malic acid, tartaric acid, aspartic acid, trichloroacetic acid, or trifluoroacetic acid; and a salt with a sulfonic acid such as methanesulfonic acid, benzenesulfonic acid, p-toluenesulfonic acid, mesitylenesulfonic acid, or naphthalenesulfonic acid.

Examples of the salt of the acidic group include a salt with an alkali metal such as sodium or potassium; a salt with an alkaline earth metal such as calcium or magnesium; an ammonium salt; and a salt with a nitrogen-containing organic base such as trimethylamine, triethylamine, tributylamine, pyridine, N,N-dimethylaniline, N-methylpiperidin, N-methylmorpholine, diethylamine, dicyclohexylamine, procaine, dibenzylamine, N-benzyl-β-phenethylamine, 1-ephenamine, or N,N'-dibenzylethylenediamine.

Among the above salts, examples of the preferred salt include a pharmacologically acceptable salt.

In a case where isomers (for example, optical isomers, geometric isomers, and tautomers) are present in the compound represented by General Formula (1), isomers thereof are included, and solvates, hydrates, and crystals of various shapes are included in the present invention.

The compound represented by General Formula (1) can be produced, for example, according to the production method described in WO2014/069510A, but the method is not limited thereto.

As the DHODH inhibitor compound, one kind of compound may be used, or two or more kinds of compounds may be used.

The daily dose of the DHODH inhibitor compound is preferably 1 mg to 500 mg, more preferably 10 mg to 400 mg, and still more preferably 50 mg to 300 mg.

The DHODH inhibitor compound can be administered once a day, twice a day, three times a day, or the like, and is preferably administered once a day or twice a day.

The administration regimen of the DHODH inhibitor compound can be appropriately adjusted according to the administration regimen of cytarabine and can also be appropriately adjusted according to the type of DHODH inhibitor compound used. The administration of the DHODH inhibitor compound is preferably performed before the administration of cytarabine or simultaneously with the administration of cytarabine.

The DHODH inhibitor compound can be provided as an anti-tumor effect enhancing agent containing a DHODH inhibitor compound, which is used in combination with cytarabine.

The DHODH inhibitor compound can be provided as an anti-tumor agent containing a DHODH inhibitor compound, which is used in combination with cytarabine.

The pharmaceutical composition according to the embodiment of the invention may be a composition in which a compound or a salt thereof, which is an active ingredient, is appropriately mixed with a pharmaceutical preparation auxiliary agent such as an additive that is used for formulation.

The pharmaceutical composition according to the embodiment of the invention may contain other active ingredients and can be used together with a drug containing other active ingredients.

Examples of the additive include an excipient, a disintegrating agent, a binder, a lubricant, a taste modifier, a coloring agent, a flavoring agent, a surfactant, a coating agent, and a plasticizer.

Examples of the excipient include sugar alcohols such as erythritol, mannitol, xylitol, and sorbitol; sugars such as white sugar, powdered sugar, lactose, and glucose; cyclodextrins such as α-cyclodextrin, β-cyclodextrin, and sulfobutyl ether β-cyclodextrin sodium; celluloses such as crystalline cellulose and microcrystalline cellulose; and starches such as corn starch, potato starch, and pregelatinized starch.

Examples of the disintegrating agent include carmellose, carmellose calcium, croscarmellose sodium, carboxymethyl starch sodium, crospovidone, hydroxypropyl cellulose with low substitution degree, and partially pregelatinized starch.

Examples of the binder include hydroxypropyl cellulose, sodium carmellose, and methyl cellulose.

Examples of the lubricant include stearic acid, magnesium stearate, calcium stearate, talc, hydrous silicon dioxide, light anhydrous silicic acid, and sucrose fatty acid ester.

Examples of the taste modifier include aspartame, saccharin, stevia, thaumatin, and acesulfame potassium.

Examples of the colorant include titanium dioxide, iron sesquioxide, yellow iron sesquioxide, black iron oxide, Food Red No. 102, Food Yellow No. 4, and Food Yellow No. 5.

Examples of the flavoring agent include essential oils such as orange oil, lemon oil, peppermint oil, and pine oil; extracts such as orange extract and peppermint extract; flavors such as cherry flavor, vanilla flavor, and fruit flavor; powdered fragrances such as apple micron, banana micron, peach micron, strawberry micron, and orange micron; vanillin; and ethyl vanillin.

Examples of the surfactant include sodium lauryl sulfate, sodium dioctyl sulfosuccinate, polysorbate, and polyoxyethylene hydrogenated castor oil.

Examples of the coating agent include hydroxypropylmethyl cellulose, aminoalkyl methacrylate copolymer E, aminoalkyl methacrylate copolymer RS, ethyl cellulose, cellulose acetate phthalate, hydroxypropyl methyl cellulose phthalate, methacrylic acid copolymer L, methacrylic acid copolymer LD, and methacrylic acid copolymer S.

Examples of the plasticizer include triethyl citrate, macrogol, triacetin, and propylene glycol.

These additives may be used alone or in a combination of two or more thereof.

The blending amount is not particularly limited, and blending may be performed appropriately so that the effect thereof is sufficiently exhibited according to each purpose.

These can be administered orally or parenterally in the form of a tablet, a capsule, a powdered drug, a syrup, a granule, a pill, a suspension, an emulsion, a liquid, a powder pharmaceutical preparation, a suppository, an eye drop, a nasal drop, an ear drop, a patch, an ointment, or an injection agent according to conventional methods. In addition, the administration method, the dose and frequency of administration can be appropriately selected according to the age, body weight, and the symptom of the patient.

EXAMPLES

The present invention will be described with reference to Examples, but the present invention is not limited thereto.

As test compounds, 5-cyclopropyl-2-((1-phenyl-1H-indol-5-yl)amino) nicotinic acid (also referred to as FLA3527), which is a DHODH inhibitor compound, ASLAN003 (2-((3,5-difluoro-3'-methoxybiphenyl-4-yl) amino) nicotinic acid), and BAY2402234 (N-(2-chloro-6-fluorophenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy} benzamide) were used. FLA3527 was produced according to the production method described in WO2014/069510A. ASLAN003 was produced according to the production method described in WO2008/077639A. BAY2402234 was produced according to the production method described in WO2018/077923A.

Test Example 1: Enzyme Reaction Inhibition Test

The DHODH enzyme assay was performed with reference to "Benjamin Bader, Wolfgang Knecht, Markus Fries, and Monika Loffler. Expression, Purification, and Characterization of Histidine-Tagged Rat and Human Flavoenzyme Dihydroorotate Dehydrogenase. Protein Expression and Purification, 1998, 13, 414 to 422."

The DHODH activity was evaluated using an enzyme assay system that is coupled with an assay in which a blue-coloring dye 2,6-dichlorophenol indophenol (DCIP, MPBIOMEDICALS, MP150118) is quenched. Purified recombinant human DHODH (DHODH, 31-395 aa, Human, His tag, *E. coli*, ATGP1615) was purchased from ATGen Co. Ltd. Enzyme assay was performed in a 384-well plate using a buffer solution obtained by adjusting the pH to 8.0 by adding 5 N potassium hydroxide (FUJIFILM Wako Pure Chemical Corporation, 168-21815) to a solution of 100 mM Hepes (Dojindo Molecular Technologies. Inc., 342-01375), 400 mM NaCl (FUJIFILM Wako Pure Chemical Corporation, 191-01665), 10% Glycerol (FUJIFILM Wako Pure Chemical Corporation, 075-00616), 0.05% Triton X-100 (Sigma-Aldrich Co., LLC, T8787-100ML), 0.2 mM, Ubiquinone-10 (FUJIFILM Wako Pure Chemical Corporation, 216-00761), 0.1 mM DHO (Sigma-Aldrich Co., LLC, D7128), 0.5% DMSO (FUJIFILM Wako Pure Chemical Corporation, 047-29353), 0.175 µg/mL DHODH, and 0.12 mM DCIP. A test compound with a predetermined concentration was added using Biomek NX (Beckman Coulter Inc.), and the enzymatic reaction was started by adding the substrate. Enzyme activity was assessed by measuring the decrease in DCIP absorbance (600 nm) for 50 minutes using an Envision plate-reading spectrophotometer (PerkinElmer, Inc.).

The enzyme reaction inhibition rate at each test compound concentration was determined, and the 50% enzyme reaction inhibition concentration [IC50 (µmol/L)] was calculated using XLfit.

Enzyme reaction inhibition rate (%)=(light emission amount of test compound-added well)/(light emission amount of DMSO-added well)×100

Figure 1:
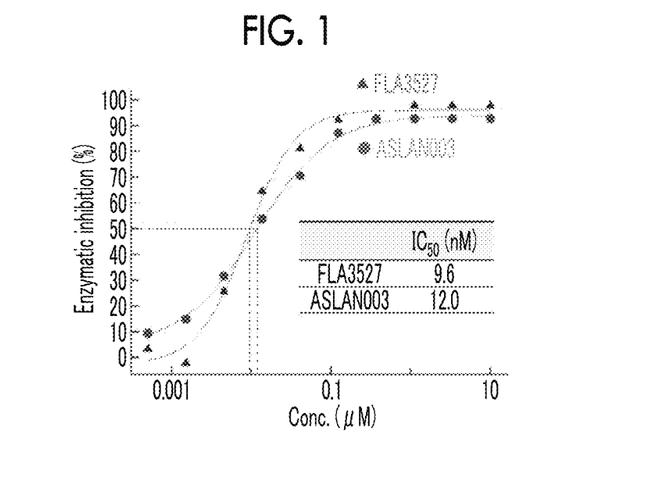
FIG. 1 shows the results of the enzyme reaction inhibitory action of each of DHODH inhibitor compounds (FLA3527, ASLAN003).

As shown in FIG. 1, each test compound showed an excellent enzyme reaction inhibitory action.

Test Example 2: Cell Proliferation Test

The cell proliferation test was performed using human myeloid leukemia cell line U-937 (ATCC, CRL-1593.2), MOLM-13 (DSMZ, ACC 554), HL60 (ATCC, CRL-240), SKM-1 (JCRB cell bank, JCRB0118), OCI-M2 (DSMZ, ACC 619), NOMO-1 (JCRB cell bank, IFO050474), MV4-11 (ATCC, CRL-9591), THP1 (ATCC, TIB-202), and human peripheral blood mononuclear cell PBMC (CTL, CTL-UP-1). As the culture medium of U-937 cells, MOLM-13 cells, HL60 cells, SKM-1 cells, OCI-M2 cells, NOMO-1 cells, MV4-11 cells, and THP1 cells, RPMI1640 (FUJIFILM Wako Pure Chemical Corporation, 189-02025) added with 10% fetal bovine serum (Thermo Fisher Scientific, Inc., 10437-028) and 1% penicillin-streptomycin (10,000 U/mL, Thermo Fisher Scientific, Inc., 15140-122) was used. As the culture medium of PBMC cells, RPMI1640 (Thermo Fisher Scientific, Inc., 11875-093) added with 10% fetal bovine serum (Thermo Fisher Scientific, Inc., 10427-028) and 1% penicillin-streptomycin (10,000 U/mL, Thermo Fisher Scientific, Inc., 15140-122) was used. U-937 cells, MOLM-13 cells, HL60 cells, SKM-1 cells, OCI-M2 cells, NOMO-1 cells, MV4-11 cells, THP1 cells, or PBMC cells were plated at 1,000 cells/20 µL/well in a 384-well plate (Corning Inc., 4588). After culturing overnight, 5 µL of FLA3527, ASLAN003, BAY2402234, or cytarabine (Ara-C, $C_{2035}$, Tokyo Chemical Industry Co., Ltd.) at the predetermined concentration was added, and 3 days later, 25 µL of Cell Titer-Glo (registered trade mark) luminescent cell viability assay (Promega Corporation, G7573) was added, and the light emission amount was measured using an Envision plate reader (PerkinElmer, Inc.). Since the light emission amount is proportional to the intracellular concentration of adenosine triphosphate (ATP), the light emission amount was used as an index of the number of living cells. The proliferation inhibition concentration for each compound concentration was calculated by the following expression.

The proliferation inhibition rate at each compound concentration was determined, and the 50% proliferation inhibition concentration [GI50 (µmol/L)] was calculated using XLfit.

Proliferation inhibition rate (%)=(light emission amount of test compound-added well)/(light emission amount of DMSO-added well)×100

The CI indicating the combined effect of Ara-C and the DHODH inhibitor compound was calculated using the software CalcuSyn of Biosoft.

Figure 2:
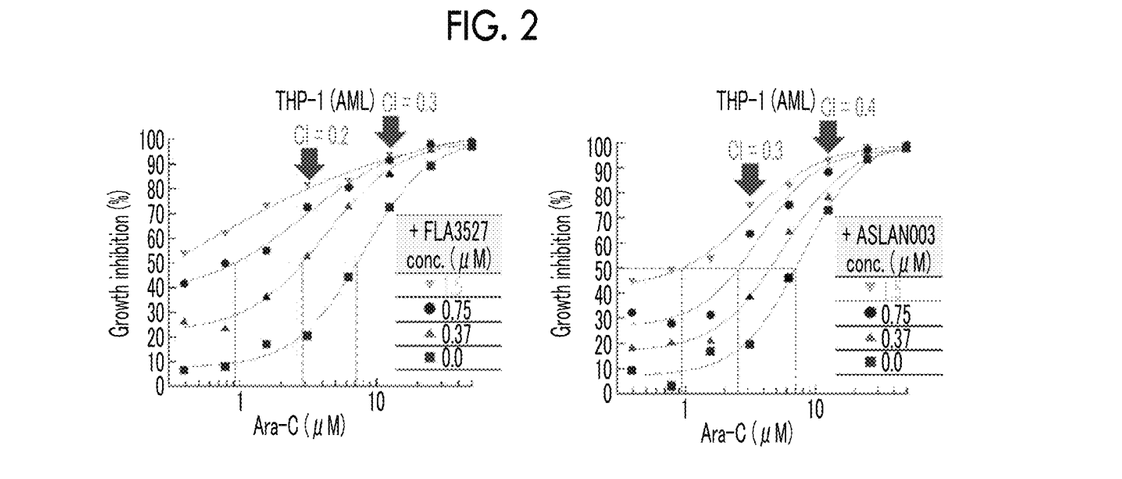
FIG. 2 shows the results of the proliferation inhibitory action of a combination of cytarabine and a DHODH inhibitor compound (FLA3527, ASLAN003) in human myeloid leukemia cell line THP1.
Figure 5:
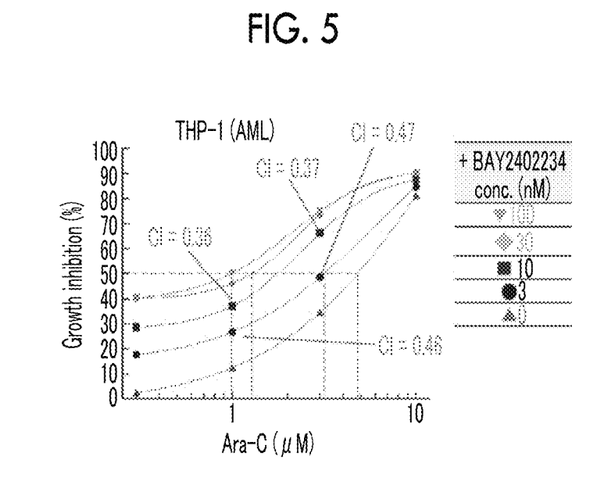
FIG. 5 shows the results of the proliferation inhibitory action of a combination of cytarabine and a DHODH inhibitor compound (BAY2402234) in human myeloid leukemia cell line THP1.

As shown in FIGS. 2 and 5, the combination of Ara-C and each test compound exhibited an excellent proliferation inhibitory action (synergistic effect) in the human myeloid leukemia cell line THP1 with a CI of 1 or less.

Figure 3:
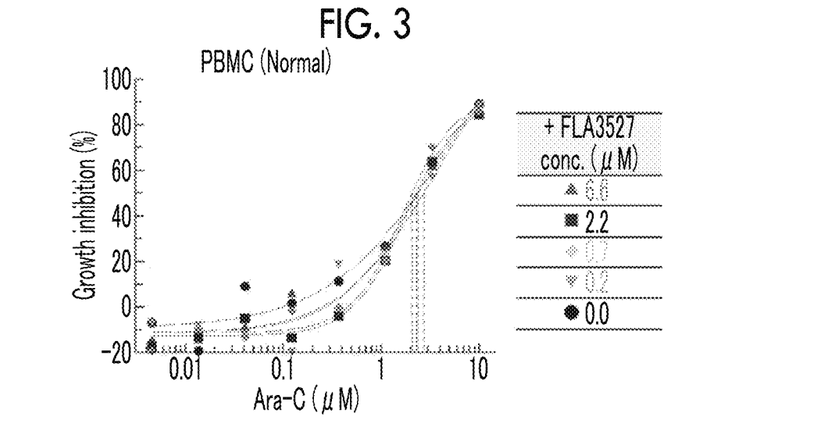
FIG. 3 shows the results of the proliferation inhibitory action of a combination of cytarabine and a DHODH inhibitor compound (FLA3527) in human peripheral blood mononuclear cell PBMC.

As shown in FIG. 3, the combination of Ara-C and each test compound did not significantly affect the human peripheral blood mononuclear cell PBMC, which is a normal cell, and thus exhibited excellent safety.

Test Example 3: Extraction of Intracellular Metabolites

THP-1 cells ($2.5 \times 10^6$ cells in a 5 ml medium) were exposed to 20 µM FLA3527 or a vehicle (DMSO) for 24 hours with 10 µM [$^{13}C_3$] AraC (Cytarabine-$^{13}C3$, C998102, TORONTO RESEARCH CHEMICALS INC.) being added to the last 4 hours. The THP-1 cell suspension was centrifuged at 1,000 rpm for 5 min (swing rotor LC-200, TOMY SEIKO Co., Ltd.) to remove the supernatant. Cells were resuspended in 10 ml PBS for washing and centrifuged at 1,000 rpm for 5 min to remove the supernatant. Next, 1 ml of PBS was added to the cells and after resuspension, 60 µl of this cell suspension was aliquoted into a 1.5 ml tube to prepare a sample for cell number measurement. 1 ml from the remaining cell suspension was aliquoted in a 1.5 ml tube for metabolite extraction. The aliquoted cell suspension was centrifuged at 2,000×g at 4° C. for 2 min and the supernatant of 900 µl was removed. For extracting the metabolites, 500 µl of methanol was added to the suspension and then well suspended. Further, 190 µl of distilled water and 10 µl of an internal standard (IS) mixture (100 µM of each of [$^{13}C_{10}$, $^{15}N_5$] dATP, [$^{13}C_{10}$, $^{15}N_5$] dGTP, [$^{13}C_9$, $^{15}N_3$] dCTP, [$^{13}C_{10}$, $^{15}N_2$] dTTP, [$^{13}C_{10}$, $^{15}N_5$] ATP, [$^{13}C_{10}$, $^{15}N_5$] GTP, [$^{13}C_9$, $^{15}N_3$] CTP, and [$^{13}C_9$, $^{15}N_2$] UTP) were added and suspended. Thereafter, the suspension was centrifuged at 10,000×g at 4° C. for 15 min, and the supernatant of 700 µl was collected in a new 1.5 ml tube. The collected supernatant was evaporated and dried at 37° C. using a centrifugal evaporator CVE-3100 (TOKYO RIKAKIKAI Co, Ltd.). The sample was then used for LC/MS/MS analysis.

[Measurement of Cell Number]

A sample diluted 10-fold with PBS was mixed with 9.5 ml of Coulter Isoton II diluent (Beckman Coulter Inc.), and 500 µl of the mixture was used to measure the cell density by Z2 Coulter counter (Beckman Coulter Inc.). The number of cells used for metabolite extraction was calculated by the following expression.

Number of cells used for metabolite extraction=Cell density×2 (counts/ml)×100 (dilution factor of Isoton)×10 (dilution factor of PBS)×1 (ml, volume of cell suspension aliquoted for extraction)

[High Performance Liquid Chromatography Tandem Mass Spectrometer (LC/MS/MS) Analysis]

The sample that had been evaporated and dried was added in 100 µl solution (a mixture of 10 mM ammonium bicarbonate and acetonitrile with a volume ratio of 35:65) and solubilized by vortexing. After centrifuging at 15,000 rpm (MX-301, TOMY SEIKO Co., Ltd.) for 5 min, 70 µl of the supernatant was collected in a vial. Acquity TQ-Detector (Waters Corporation) was used for LC/MS/MS analysis. A 10 µl of a sample was developed on a SeQuant ZIC-pHILIC 5 µm 150×4.6 mm PEEK coated HPLC column (Merck Millipore) at a flow rate of 0.5 ml/min and then eluted as follows (eluent A: 10 mM ammonium bicarbonate/0.05% aqueous ammonia, eluent B: acetonitrile. 0 to 5 min: linear gradient from 65% B to 40% B, 5 to 7 min: linear gradient to 0% B, 7 to 9 min: 0% B isocratic, 9 to 9.1 min: linear gradient to 65% B, 9.1 to 15 min: 65% B isocratic). The multiple reaction monitoring (MRM) conditions for MS analysis are shown in Table 1. The amount of each metabolite was calculated from the peak area ratio of the metabolite and IS thereof. The standard product of each metabolite and IS of each metabolite were used to prepare the calibration curve. [$^{13}C_3$] AraCTP was relatively quantified by the peak area ratio of [$^{13}C_3$] AraCTP to CTP IS without using the calibration curve since the standard product thereof was not present.

Figure 4:
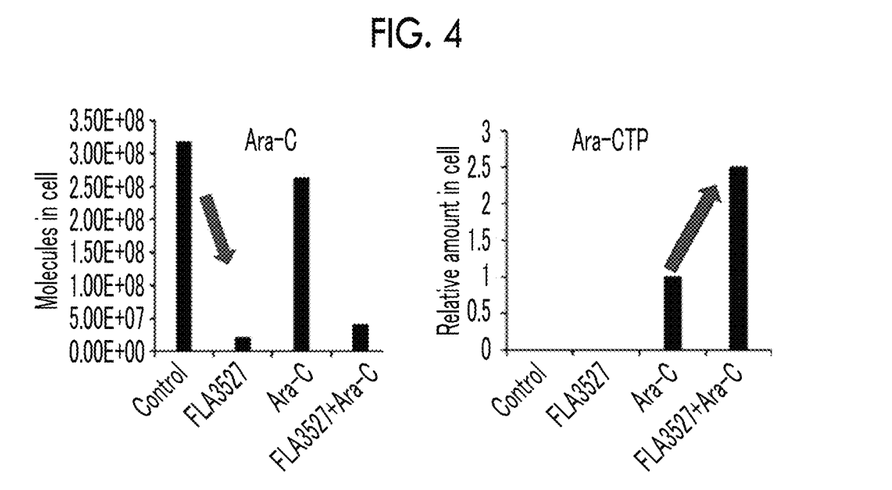
FIG. 4 shows changes in CTP concentration and Ara-CTP concentration due to treatment with a DHODH inhibitor compound (FLA3527).

As shown in FIG. 4, a significant decrease in CTP concentration was observed by treatment with the DHODH inhibitor compound. In addition, in a case where Ara-C was used in combination with the DHODH inhibitor compound, the same effect as the decrease in CTP concentration in a case where the DHODH inhibitor compound was treated alone was observed. On the other hand, the treatment with the DHODH inhibitor compound increased the Ara-CTP concentration by about 2.5 times as compared with the case of Ara-C alone.

Test Example 4: RNA Quantification Test Using Quantitative PCR (qPCR) Method $1.2 \times 10^6$ cells/well of U-937 cells, MOLM-13 cells, HL60 cells, SKM-1 cells, OCI-M2 cells, NOMO-1 cells, MV4-11 cells, THP1 cells were plated in a 6-well plate (Corning Inc., 3506), washed with PBS after 24 hours, and collected. RNA was extracted using RNeasy kit (QIAGEN, 74106), and RNA concentration was measured with Nanodrop (Thermo Fisher Scientific, Inc., ND-1000). cDNA was synthesized using the Super Script VILO cDNA Synthesis Kit (Invitrogen, 11754-250) using the extracted RNA as the template according to the specified protocol. The PCR reaction was performed under the conditions of 25° C. for 10 minutes, 42° C. for 60 minutes, and 85° C. for 5 minutes.

The synthesized cDNA was mixed with Taqman Universal PCR Master Mix (Applied Biosystems, 4369016) and a Taqman Probe (Applied Biosystems, Hs00210019_m1) for SAMHD1 mRNA (cDNA), and qPCR measurement was performed with the MX3000P real-time quantitative PCR system (Stratagene). GAPDH Taqman Probe (Thermo Fisher Scientific, Inc., 4310884E) was used as an internal control gene. The relative quantification method (ΔΔCt method) was used to quantify mRNA, and the relative expression levels between the samples were compared.

Figure 6:
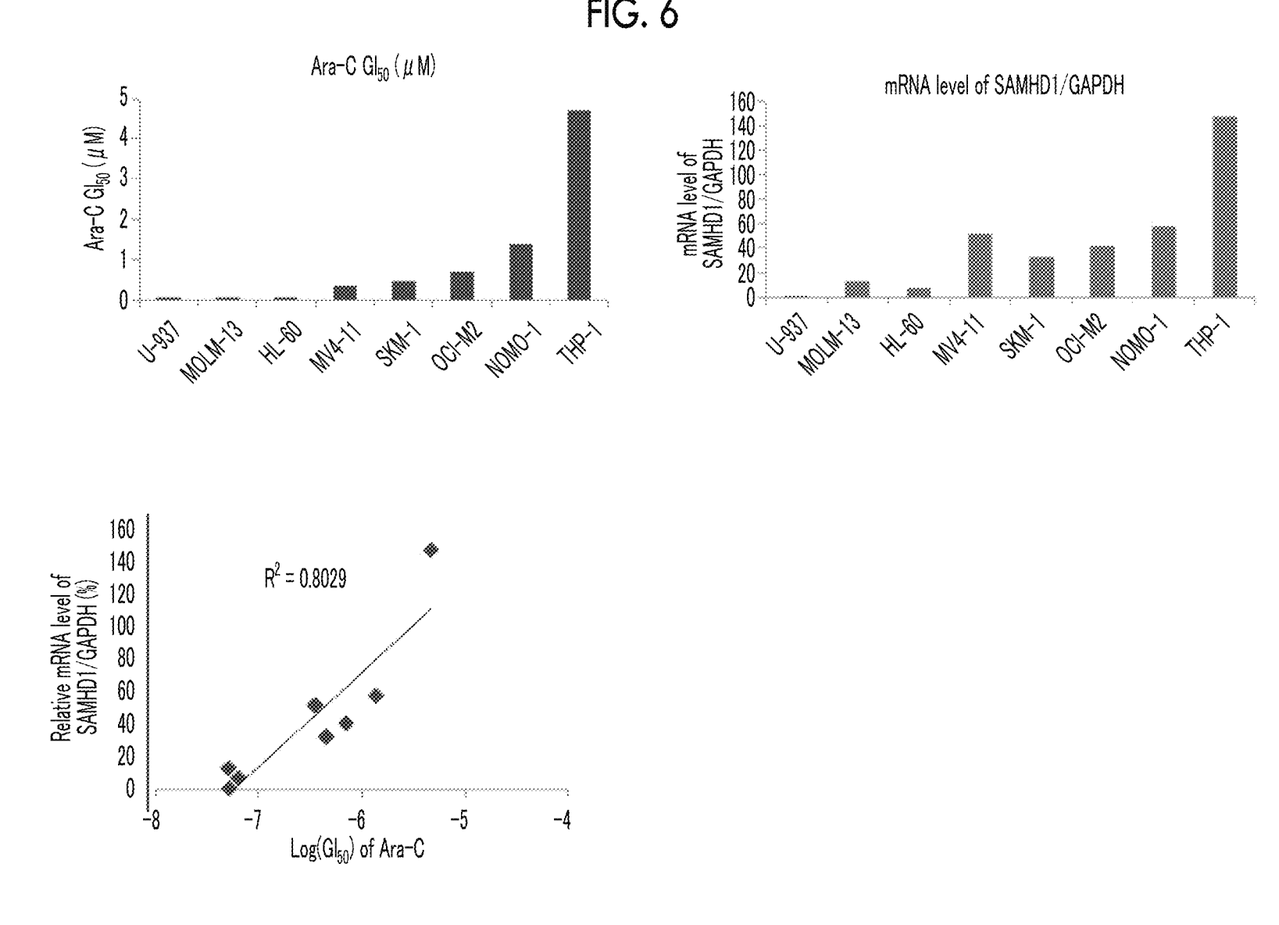
FIG. 6 shows the results of the correlation between Ara-C GI50 and SAMHD1 mRNA level in AML cells.

As shown in FIG. 6, when the Ara-C GI50 and the mRNA level of SAMHD1 between AML cells were compared, various Ara-C sensitivity and SAMHD1 expression patterns were shown. In various cell lines, when the Ara-C GI50 was Log-converted and plotted on the X-axis and the mRNA level of SAMHD1 was plotted on the Y-axis, a strong correlation was shown with a correlation coefficient $R^2=0.8029$. It is known from FIG. 1 on p. 251 of Nature Medicine volume 23, pages 251 to 255 (2017) that SAMHD1 expression and the drug efficacy of Ara-C are inversely correlated in AML cell lines. The results of the present study have confirmed the correlation between SAMHD1 expression and Ara-C drug efficacy.

Figure 7:
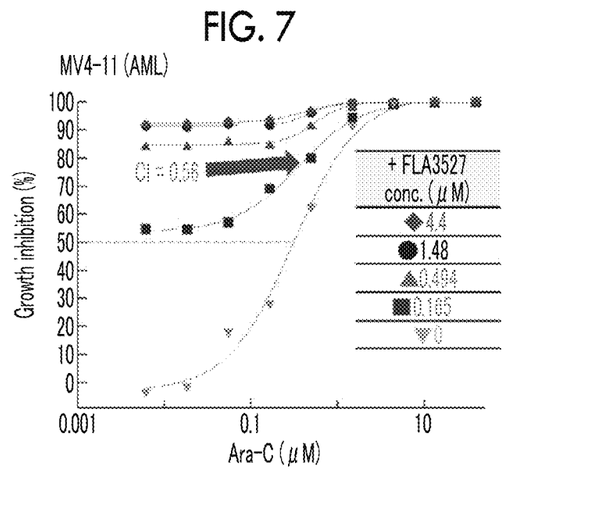
FIG. 7 shows the results of the proliferation inhibitory action of a combination of cytarabine and a DHODH inhibitor compound (FLA3527) in human myeloid leukemia cell line MV4-11.

As shown in FIG. 7, in the human myeloid leukemia cell line MV4-11 which is sensitive to Ara-C and in which the SAMHD1 expression level is moderate, the combined use of Ara-C and a DHODH inhibitor compound had a CI of 1 or less (0.56) and a synergistic effect was observed. As compared with CI (0.2 to 0.4, in FIG. 2) in THP1 cells having the highest SAMHD1 expression level, the synergistic effect was low, indicating that SAMHD1 expression correlates with the effect of combined use of Ara-C and the DHODH inhibitor compound.

The combination drug containing cytarabine and the DHODH inhibitor compound according to the embodiment of the invention is useful as a new anti-tumor agent.

What is claimed is:

1. A method for treating a tumor, including administering cytarabine and a dihydroorotate dehydrogenase inhibitor compound to a subject,
wherein the tumor cells are cytarabine-resistant leukemia cells; and
the dihydroorotate dehydrogenase inhibitor compound is at least one or more compounds selected from the group consisting of Brequinar, Vidofludimus, Teriflunomide, Leflunomide, N-(2-chloro-6-fluorophenyl)-4-[4-ethyl-3-(hydroxymethyl)-5-oxo-4,5-dihydro-1H-1,2,4-triazol-1-yl]-5-fluoro-2-{[(2 S)-1,1,1-trifluoropropan-2-yl] oxy} benzamide, (S)-4-chlorophenyl 6-chloro-1-(4-hydroxyphenyl)-3,4-dihydro-1H-pyrido[3,4-b]indol-2 (9H)-carboxylate, and a compound represented by General Formula (1), or a salt thereof, (1)

in the formula,
$G^1$ is a CH or nitrogen atom;
$R^1$ is a hydrogen atom, a halogen atom, a $C_{1-6}$ alkyl group which may be substituted, or a $C_{3-8}$ cycloalkyl group which may be substituted; and
$R^2$ is an aryl group which may be substituted or a bicyclic heterocyclic group which may be substituted, or
the dihydroorotate dehydrogenase inhibitor compound is at least one or more compounds selected from the group consisting of ASLAN003 (2-((3,5-difluoro-3'-methoxybiphenyl-4-yl)amino) nicotinic acid) and 5-cyclopropyl-2-((1-phenyl-1H-indol-5-yl)amino) nicotinic acid, or a salt thereof.

2. The method for treating a tumor according to claim 1, wherein the tumor is acute lymphocytic leukemia (ALL), acute myelogenous leukemia (AML), acute promyelocytic leukemia (APL), chronic lymphocytic leukemia (CLL), chronic myelogenous leukemia (CML), chronic neutrophilic leukemia (CNL), acute undifferentiated leukemia (AUL), anaplastic large cell lymphoma (ALCL), prolymphocytic leukemia (PML), juvenile myelomonocytic leukemia (JMML), adult T-cell leukemia (ATL), myelodysplastic syndrome (MDS), myeloproliferative disease (MPD), lymphoblastic lymphoma (LBL), or adult T-cell leukemia/lymphoma (ATL).

3. The method for treating a tumor according to claim 1, wherein the tumor is acute lymphocytic leukemia (ALL), acute myelogenous leukemia (AML), acute promyelocytic leukemia (APL), or chronic myelogenous leukemia (CML).

4. The method for treating a tumor according to claim 1, wherein a daily dose of the cytarabine is 1 g/m² to 10 g/m².

5. A method for enhancing an anti-tumor effect, including administering a dihydroorotate dehydrogenase inhibitor compound to a subject in combination with cytarabine,
wherein the tumor cells are cytarabine-resistant leukemia cells; and
the dihydroorotate dehydrogenase inhibitor compound is at least one or more compounds selected from the group consisting of Brequinar, Vidofludimus, Teriflunomide, Leflunomide, N-(2-chloro-6-fluorophenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy} benzamide, (S)-4-chlorophenyl 6-chloro-1-(4-hydroxyphenyl)-3,4-dihydro-1H-pyrido[3,4-b]indol-2(9H)-carboxylate, and a compound represented by General Formula (1), or a salt thereof, (1)

in the formula,
$G^1$ is a CH or nitrogen atom;
$R^1$ is a hydrogen atom, a halogen atom, a $C_{1-6}$ alkyl group which may be substituted, or a $C_{3-8}$ cycloalkyl group which may be substituted; and
$R^2$ is an aryl group which may be substituted or a bicyclic heterocyclic group which may be substituted, or
the dihydroorotate dehydrogenase inhibitor compound is at least one or more compounds selected from the group consisting of ASLAN003 (2-((3,5-difluoro-3'-methoxybiphenyl-4-yl)amino) nicotinic acid) and 5-cyclopropyl-2-((1-phenyl-1H-indol-5-yl)amino) nicotinic acid, or a salt thereof.

* * * * *